(12) United States Patent
Nakagawa

(10) Patent No.: US 7,124,623 B2
(45) Date of Patent: Oct. 24, 2006

(54) GAS SENSOR

(75) Inventor: Kazuya Nakagawa, Kariya (JP)

(73) Assignee: Denso Corporation(JP)

( * ) Notice: Subject to any disclaimer, the term of this patent is extended or adjusted under 35 U.S.C. 154(b) by 41 days.

(21) Appl. No.: 11/017,003

(22) Filed: Dec. 21, 2004

(65) Prior Publication Data

US 2005/0132778 A1 Jun. 23, 2005

(30) Foreign Application Priority Data

Dec. 22, 2003 (JP) ............................. 2003-425644

(51) Int. Cl.
*G01N 9/00* (2006.01)
*G01N 7/00* (2006.01)

(52) U.S. Cl. ..................... 73/23.31; 73/31.05; 204/424

(58) Field of Classification Search ............... 73/23.31, 73/23.32, 31.05; 204/424, 425, 426, 427, 204/428, 429
See application file for complete search history.

(56) References Cited

U.S. PATENT DOCUMENTS

| | | | |
|---|---|---|---|
| 3,936,794 A * | 2/1976 | Beaudoin et al. ............. 338/34 |
| 4,038,034 A | 7/1977 | Nakajima et al. |
| 4,177,125 A * | 12/1979 | Barnabe ...................... 204/424 |
| 4,383,907 A * | 5/1983 | Legrand et al. ............. 204/426 |
| 4,403,207 A | 9/1983 | Murphy et al. |
| 4,596,975 A * | 6/1986 | Reddy et al. ................. 338/34 |
| 4,606,807 A * | 8/1986 | Mendenhall ................ 204/433 |
| 2002/0053233 A1 | 5/2002 | Grieser et al. ............. 73/31.05 |

FOREIGN PATENT DOCUMENTS

DE 43 12 506 10/1994
EP 0 822 410 2/1998

OTHER PUBLICATIONS

Chinese Official Action dated Jul. 21, 2006 issued in corresponding Chinese Appln. No. 2004101036806 with English translation.

* cited by examiner

*Primary Examiner*—Michael Cygan
(74) *Attorney, Agent, or Firm*—Nixon & Vanderhye PC

(57) ABSTRACT

A gas sensor having a first end and a second end includes a hollow cylindrical housing having a flange which protrudes from outer periphery thereof, a sensing element fixed in the housing, and a heat conduction inhibitor disposed on a first end of the flange so as to prevent deterioration of parts of the gas sensor by decreasing heat conduction through the gas sensor.

20 Claims, 7 Drawing Sheets

GAS SENSOR

CROSS REFERENCE TO RELATED APPLICATION

This application is based on Japanese Patent Application No. 2003-425644 filed on Dec. 22, 2003, the disclosure of which is incorporated herein by reference.

FIELD OF THE INVENTION

The present invention relates to a gas sensor for measuring a concentration of a specified gas contained in exhaust gasses of an internal combustion engine.

BACKGROUND OF THE INVENTION

Conventionally, a gas sensor is installed in an exhaust pipe of an internal combustion engine to measure a concentration of a specified gas, for example Oxygen or NOx, in exhaust gasses.

FIG. 15 shows an example of such a gas sensor. A gas sensor 9 includes a hollow cylindrical housing 10 having a flange 100, a sensing element 19 fixed in the housing 10, a protective cover 11 disposed on a first end of the housing 10, and an outer cover 12 disposed on a second end of the housing 10. A first end of the gas sensor 9 is inserted into a fitting hole 30 formed in an exhaust pipe 3. A washer 102 is disposed between a first end 101 of the flange 100 and an outer surface 301 around the fitting hole 30 of the exhaust pipe 3.

Recently, the amount of heat conducted from a first end to a second end of a gas sensor has increased, since a temperature of exhaust gasses has become higher. However, a gas sensor generally includes less heat-resistant parts, for example a water-repellent filter 123 or a rubbery insulator 15 as shown in FIG. 15.

SUMMARY OF THE INVENTION

It is, therefore, an object of the present invention to provide a gas sensor having an improved structure which decreases the amount of heat conducted from a first end to a second end of a gas sensor for preventing deterioration of less heat-resistant parts.

According to one aspect of the invention, there is provided a gas sensor having a first end and a second end which comprises:

a hollow cylindrical housing having a flange which protrudes radially from an outer periphery thereof;

a sensing element fixed in the housing; and a heat conduction inhibitor disposed on a first end of the flange.

A washer may be disposed on a first end of the heat conduction inhibitor.

There are two routes of heat conduction of the gas sensor as shown in FIG. 4 and FIG. 5. The first route is from the first end to the second end of the gas sensor through the housing. The second route is from a mounting part in which a gas sensor is fixed, for example an exhaust pipe as shown in FIG. 1 and FIG. 15, to the second end of the gas sensor through the flange.

When a heat conduction inhibitor embodying the invention is disposed on the first end of the flange, the second route of heat conduction is inhibited. Therefore, the amount of heat conducted through the gas sensor of the present invention is decreased compared to that of a conventional gas sensor.

According to preferred embodiment of the present invention, the heat conduction inhibitor has a ring structure. Since an inhibitor having a ring structure can inhibit heat conduction around the entire periphery thereof, the amount of heat conducted through the gas sensor decreases. The inhibitor preferably has an inner diameter through which the first end of the housing can be inserted, so that the inhibitor contacts the first end of the flange.

The gas sensor is inserted in an exhaust pipe in which exhaust gasses flow. Thus, it is important to seal at around a fitting hole formed in an exhaust pipe for preventing outflow. According to another embodiment of the present invention, the heat conduction inhibitor has at least one protrusion on a first end and/or a second end thereof. In an exemplary embodiment, the protrusion has a low stiffness, so that the protrusion can be deformed. Therefore, the inhibitor can be used as a seal member.

According to yet another embodiment of the present invention, the heat conduction inhibitor has at least one groove in an outer periphery thereof. Since the groove inhibits heat conduction through the gas sensor, the amount of heat conducted through the gas sensor decreases.

According to an exemplary embodiment of the present invention, the heat conduction inhibitor has at least one protrusion on an outer periphery thereof. Since the protrusion radiates heat of the gas sensor, the amount of heat conducted through the gas sensor decreases.

According to another exemplary preferred embodiment of the present invention, the heat conduction inhibitor is made of stainless steel. The inhibitor being made of stainless steel has sufficient durability as an automobile part.

According to yet another embodiment of the present invention, the heat conduction inhibitor has a coefficient of thermal conductivity that is lower than that of the housing. Thus, the inhibitor decreases the amount of heat conducted through the gas sensor.

According to a further embodiment of the present invention, the heat conduction inhibitor has a thickness of equal to or greater than 0.2 mm in an axial direction of the housing. When the inhibitor has a thickness of equal to or greater than 0.2 mm in an axial direction of the housing, the inhibitor is ensured strength, heat conduction inhibiting performance and productivity. However, if the inhibitor has a thickness of greater than about 3 mm in an axial direction of the housing, a length from the first end of the inhibitor to the second end of the gas sensor is too long to fix in an exhaust pipe of an automobile. It is possible to reduce the thickness of the flange to ensure that there is sufficient space for the inhibitor. However, when the thickness of the flange is less than 3 mm, there can be trouble fixing using a tool, for example breakage of the flange or a lack of tightening torque.

The method of mounting a gas sensor of the present invention is a method employing the above-mentioned gas sensor.

BRIEF DESCRIPTION OF THE DRAWINGS

The present invention will be understood more fully from the detailed description given hereinafter and from the accompanying drawings of the preferred embodiments of the invention, which, however, should not be taken to limit the invention to the specific embodiments but are for the purpose of explanation and understanding only.

In the accompanying drawings.

DETAILED DESCRIPTION OF EMBODIMENT

An embodiment of the present invention will be described hereinafter with reference to the drawings.

Figure 1:
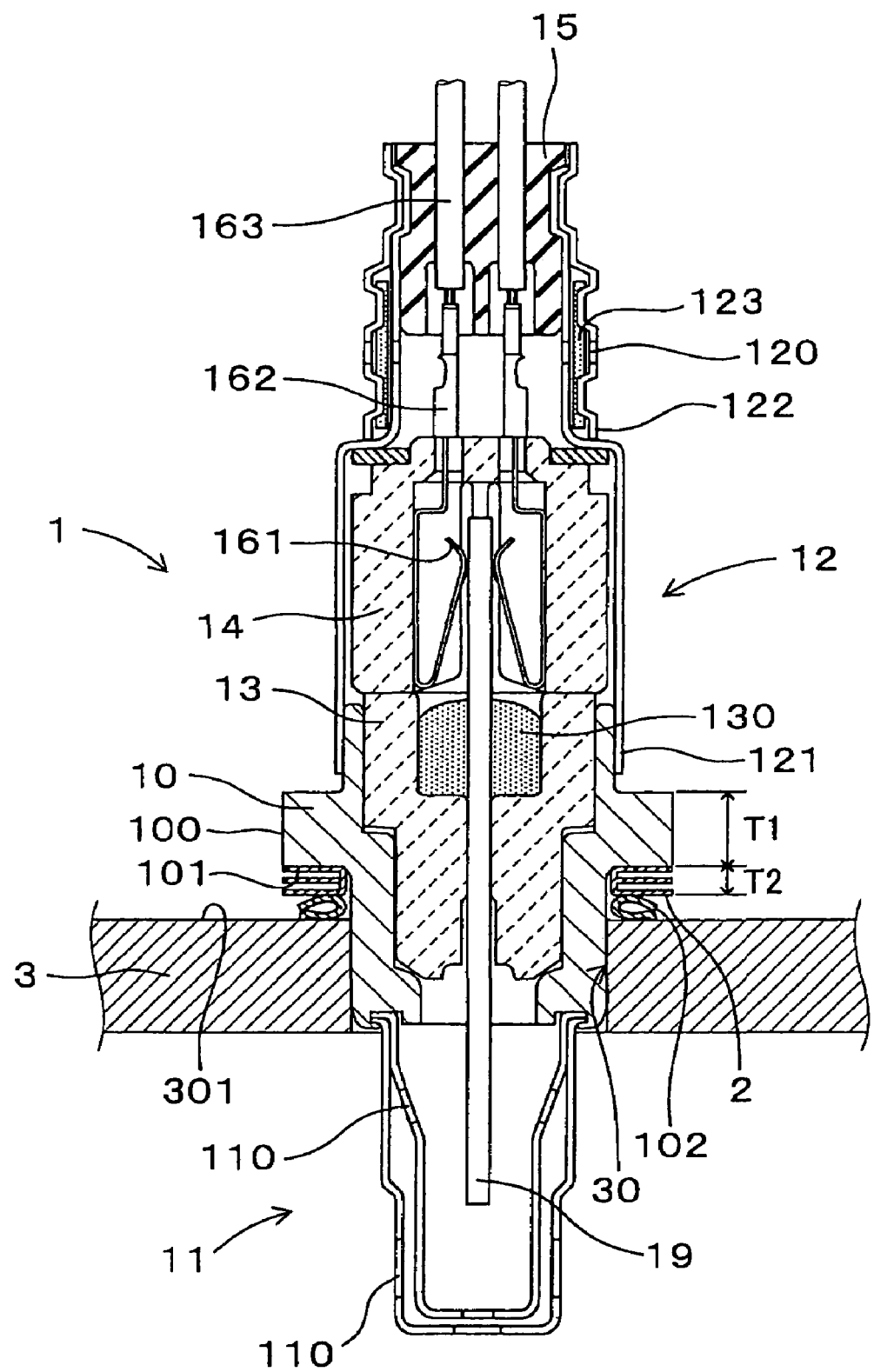
FIG. 1 is a cross sectional view showing a gas sensor according to the present invention.

As shown in FIG. 1, a gas sensor 1 having a first end and a second end includes a hollow cylindrical housing 10 having a first end and a second end, a sensing element 19 fixed in the housing 10, a protective cover 11 disposed on the first end of the housing 10, and an outer cover 12 disposed on the second end of the housing 10. The housing 10 has a flange 100 which protrudes from an outer periphery thereof. A heat conduction inhibitor 2 is disposed on a first end 101 of the flange 100. A washer 102 is disposed on a first end of the heat conduction inhibitor 2.

As shown in FIG. 1, the gas sensor 1 is fixed in a fitting hole 30 formed in an outer surface 301 of an exhaust pipe 3, which is used for emitting exhaust gasses from the internal combustion engine of an automobile, so that the protective cover 11 is disposed inside the exhaust pipe 2. The washer 102 has elasticity in the axial diameter of the gas sensor 1. The washer 102 is disposed between the housing 10 and the fitting hole 30 so that the washer 102 seals between the gas sensor 1 and the exhaust pipe 3.

As shown in FIG. 1, the protective cover 11 has an outer protective cover and an inner protective cover. Gas inlet holes 110 are formed in an outer periphery of the protective cover 11 for getting gasses into the protective cover 11. The first end of the sensing element 19 is disposed in the protective cover 11. The sensing element 19 determines a concentration of a specified gas.

The outer cover 12 has a main outer cover 121 and a filter cover 122. The main outer cover 121 is fixed, by welding, on the second end of the housing 10. The filter cover 122 is fixed, by caulking, on the second end of the main outer cover 121. A water-repellent filter 123 is disposed between the main outer cover 121 and the filter cover 122. The main outer cover 121 and the filter cover 122 have air inlet holes 120 in the side surface thereof which faces the water-repellent filter 123, for getting air into the outer cover 12.

The sensing element 19 is fixed with a seal member 130 in a first insulator 13 having a hollow cylindrical shape. The first insulator 13 is fixed in the housing 10. A second insulator 14 is disposed on a second end of the first insulator 13. A second end of the sensing element 19 and terminals 161 for sending signal of the sensing element 19 are disposed in the second insulator 14. Lead wires 163 are connected to the second end of the terminals 161 through connecting members 162 outside of the second insulator 14. The lead wires 163 extend to the outside of the gas sensor 1 through a rubbery insulator 15 which disposed in the second end of the outer cover 12.

Figure 2:
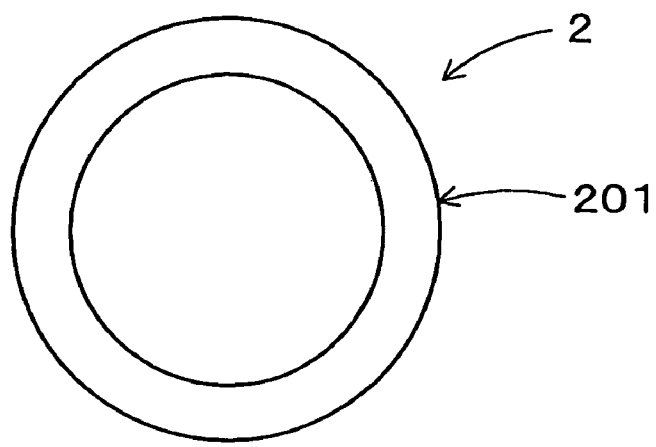
FIG. 2 is a plan view showing a heat conduction inhibitor according to the present invention.
Figure 3:
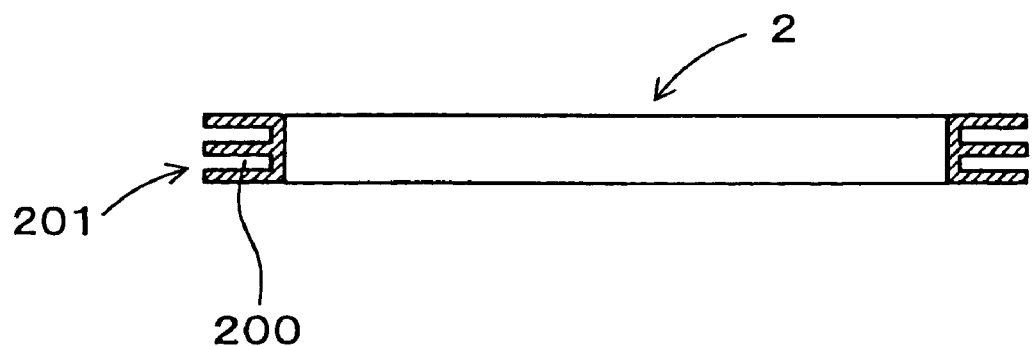
FIG. 3 is a cross sectional view showing a heat conduction inhibitor according to the present invention.

As shown in FIG. 1 to FIG. 3, in this embodiment the heat conduction inhibitor 2 has a ring structure. An outer diameter of the illustrated inhibitor 2 is approximately as large as an outer diameter of the flange 100. The inhibitor 2 has three annular grooves 200 on outer periphery 201.

The housing 10 is made of SUS430 (whose a coefficient of thermal conductivity is 26 W/m·°C.). In this embodiment the inhibitor 2 is made of SUS304 (whose a coefficient of thermal conductivity is 16.3 W/m·°C.). Thus, the coefficient of thermal conductivity of the inhibitor 2 is less than that of the housing 10. As shown in FIG. 1, a thickness T1 of the flange 100 in axial direction of the gas sensor 1 is about 3 mm$\leq$T1, for example 4 mm, and a thickness T2 of the inhibitor 2 in axial direction of the gas sensor 1 is about 0.2 mm$\leq$T2$\leq$3 mm, for example 2 mm.

Figure 15:
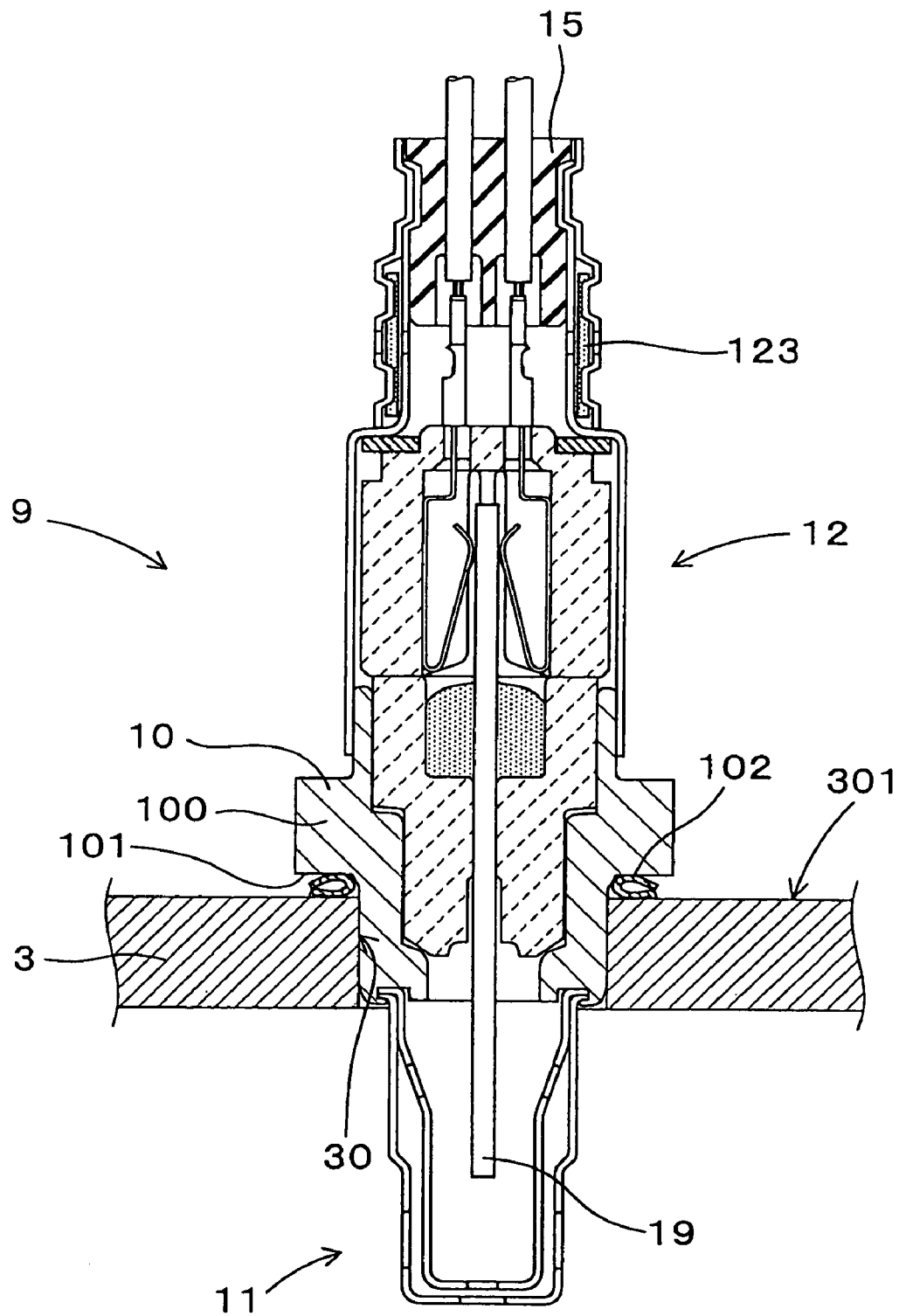
FIG. 15 is a cross sectional view showing a gas sensor according to a conventional gas sensor.

The inventor of the present invention evaluated heat conduction of the gas sensor by measuring a temperature of the housing 10 of the gas sensor 1 (FIG. 1) and a conventional gas sensor 9 (FIG. 15). The gas sensor 1 and the conventional gas sensor 9 are fixed in an electric heating furnace, simulating an exhaust pipe, so that the protective cover 11 extends into the electric heating furnace.

Figure 6:
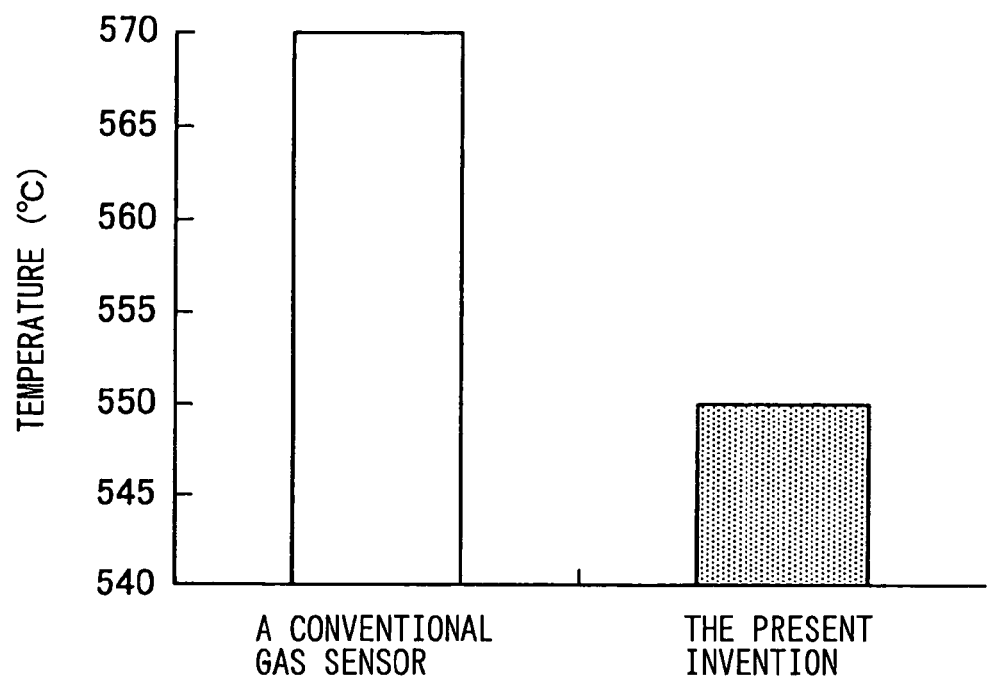
FIG. 6 is a graphical representation showing a temperature of a flange according to the present invention and in a conventional gas sensor.
Figure 7:
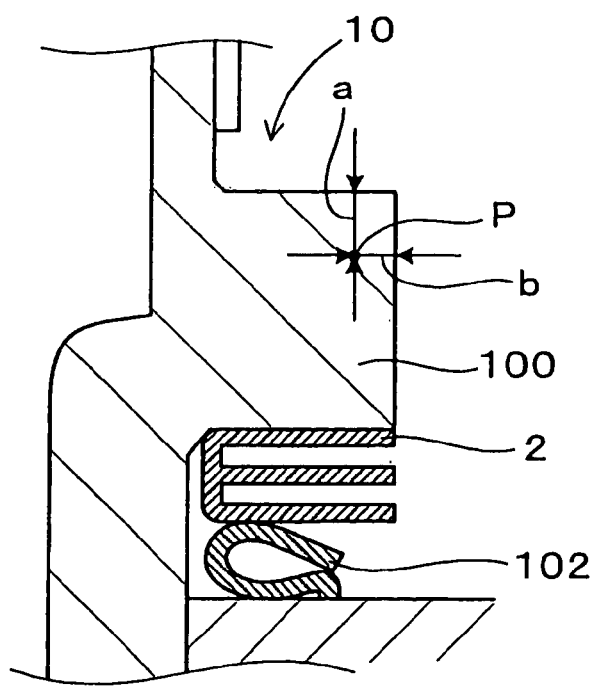
FIG. 7 is an illustration for showing a measurement point of a temperature of a flange.

As shown in FIG. 7, a thermocouple is inserted into a hole formed in the flange 100 so that the thermocouple can measure a temperature at P point, which is located at a distance of 3 mm (as "a" shown in FIG. 7) from the second end 103 of the flange 100 and located at a distance of 1 mm (as "b" shown in FIG. 7) from the outer periphery of the flange 100. FIG. 6 shows the measurement result. As can be seen from FIG. 6, the temperature of the flange 100 of the gas sensor 1 is lower than that of conventional gas sensor 9.

Figure 4:
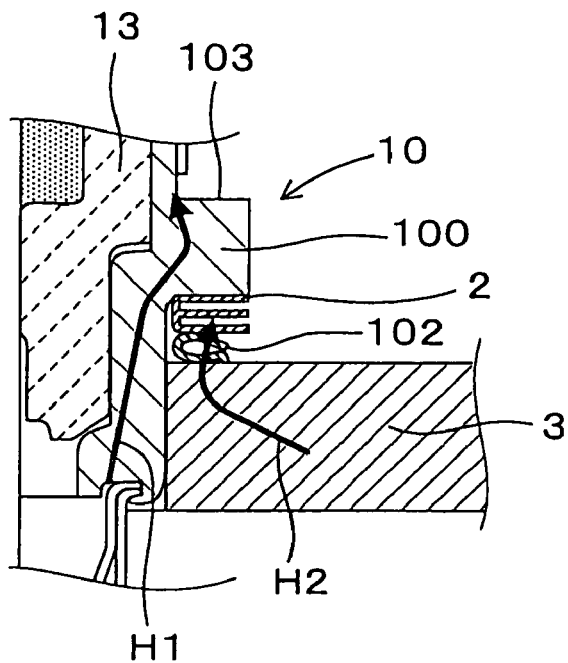
FIG. 4 is an illustration for showing routes of heat conduction according to the present invention.

FIG. 4 shows heat conduction through the gas sensor 1. At first, heat of measured gasses is conducted to the protective cover 11. Then the heat is conducted to the housing 10 along a heat conduction route H1. Heat of the exhaust pipe is conducted to the inhibitor 2 via the washer 102 along a heat conduction route H2. The washer 102 and the inhibitor 2 inhibit the heat conduction along the route H2. Furthermore, since the inhibitor 2 has grooves 200 on the outer periphery 201, the amount of the heat conducted through the gas sensor 1 is decreased.

Figure 5:
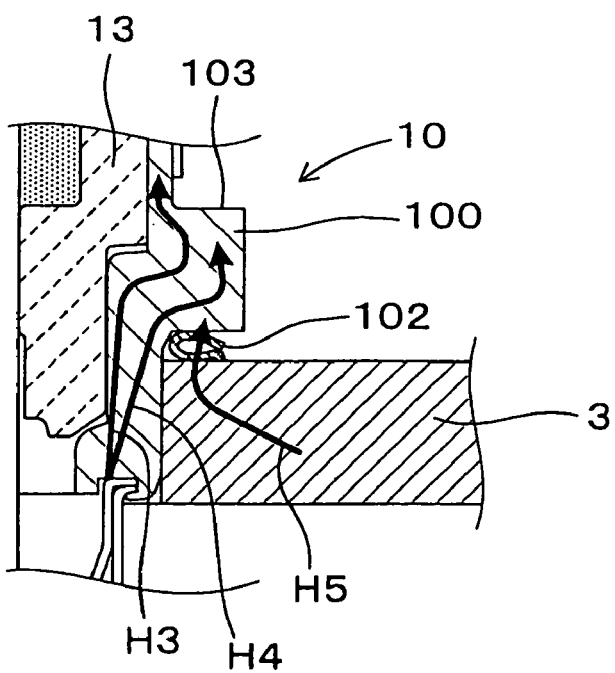
FIG. 5 is an illustration for showing routes of heat conduction according to a conventional gas sensor.

On the other hand, in the conventional gas sensor 9, heat of measured gasses is conducted from the protective cover to the housing 10 along the heat conduction route H3 and H4. Heat of the exhaust pipe is conducted to the flange 100 via the washer 102 along a heat conduction route H5, as shown in FIG. 5.

In short, since the gas sensor 1 of the present invention has the inhibitor 2, the amount of the heat conducted through the gas sensor 1 is decreased compared to that of the conventional gas sensor.

Figure 8:
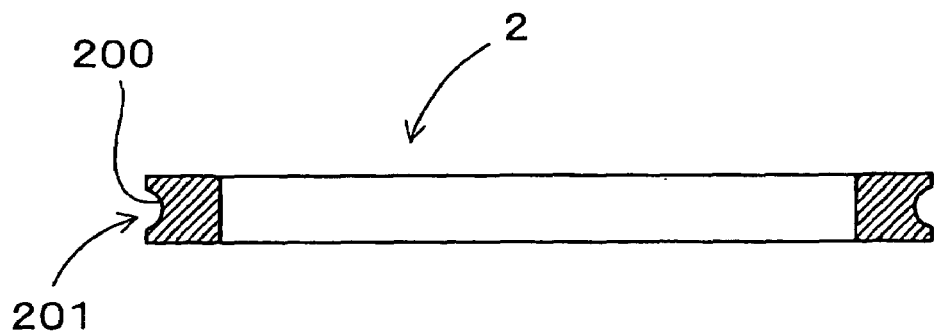
FIG. 8 is a cross sectional view showing a heat conduction inhibitor that has a groove according to the present invention.
Figure 9:
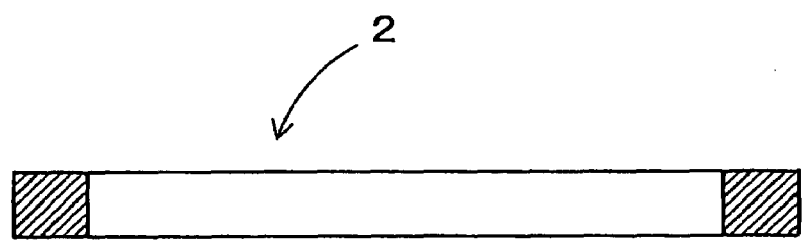
FIG. 9 is a cross sectional view showing a heat conduction inhibitor that has a simple ring structure according to the present invention.
Figure 10:
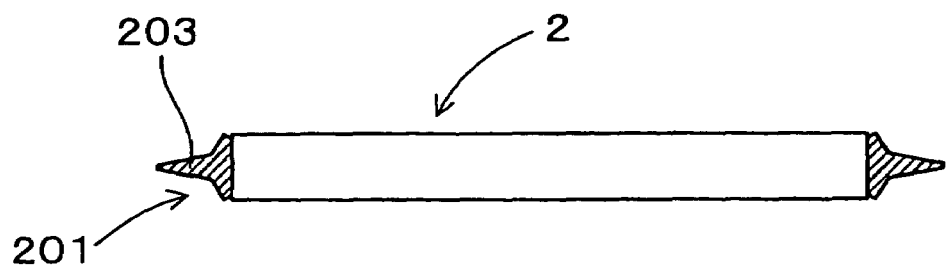
FIG. 10 is a cross sectional view showing a heat conduction inhibitor that has a protrusion on an outer periphery thereof according to the present invention.
Figure 11:
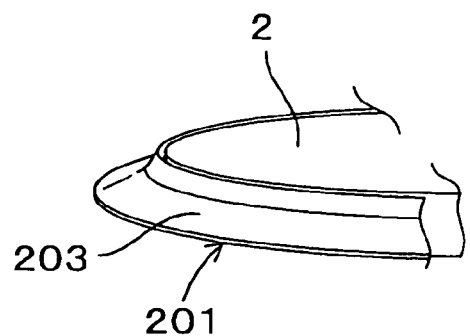
FIG. 11 is an illustration for showing a heat conduction inhibitor that has a protrusion on an outer periphery thereof according to the present invention.
Figure 12:
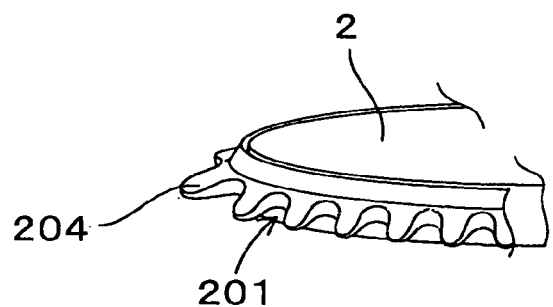
FIG. 12 is an illustration for showing a heat conduction inhibitor that has a number of protrusions on an outer periphery thereof according to the present invention.
Figure 13:
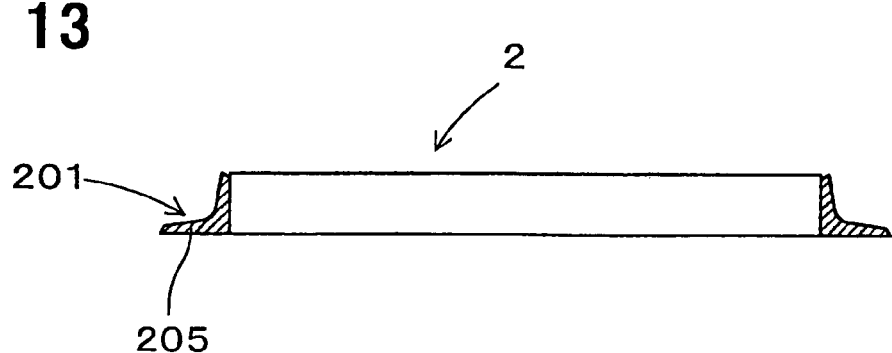
FIG. 13 is a cross sectional view showing a heat conduction inhibitor that has a protrusion on an outer periphery at a first end thereof according to the present invention.
Figure 14:
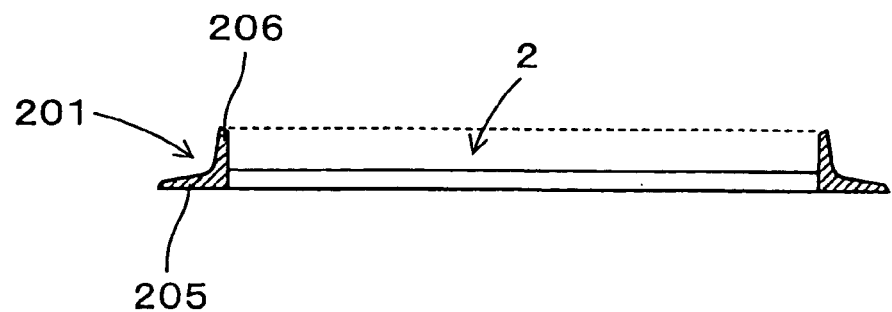
FIG. 14 is a cross sectional view showing a heat conduction inhibitor that has protrusions on a first end and a second end thereof according to the present invention.

FIG. 8 to FIG. 14 show modified structures of an inhibitor. FIG. 8 shows an inhibitor 2 having a ring structure and groove(s) 200 on an outer periphery 201. In this embodiment the groove is a circumferential groove, and only a single groove is provided, FIG. 9 shows an inhibitor 2 having a simple ring structure. FIG. 10 and FIG. 11 show an inhibitor having a ring structure and an annular protrusion 203 on an outer periphery 201. FIG. 12 shows an inhibitor having a ring structure and a number of protrusions 203 on an outer periphery 201. FIG. 13 shows an inhibitor having a ring structure and an annular protrusion 205 on outer periphery 201 at a first end thereof. A number of protrusions 203 as shown in FIG. 12 can replace the annular protrusion 205 as shown in FIG. 13. FIG. 14 shows an inhibitor having a ring structure and an annular protrusion 205 on outer periphery 201 and protrusions 206 on a second end thereof.

The inhibitors shown in FIG. 8 to FIG. 14 decrease the amount of heat conduction. Furthermore, since the protrusion(s) 203, 204 and 205 radiate heat, the gas sensor having the protrusion(s) 203, 204 and 205 decrease the amount of heat conducted more and more. The inhibitor having the protrusion(s) 206 can be used as a seal member, since the protrusions(s) 206 have a lower stiffness than the other portion of the inhibitor.

While the above particular embodiments of the invention have been shown and described, it will be understood by those who practice the invention and those skilled in the art that various modifications, changes, and improvements may be made to the invention without departing from the spirit of the disclosed concept.

For example, in the previous embodiments, the sensing element may have a cup-shaped structure or a laminated structure and may determine a concentration of the Oxygen or NOx. Moreover, except the essential dimensional relationships specified in the previous embodiments, other detailed dimensional ranges and/or relationships may be suitably modified, or changed in designing the gas sensors.

Such modifications, changes, and improvements within the skill of the art are intended to be covered by the appended claims.

Thus, the present invention should not be limited to the disclosed embodiments, but may be implemented in other ways without departing from the spirit of the invention.

What is claimed is:

1. A gas sensor having a first end and a second end comprising:
    a hollow cylindrical housing having a flange which protrudes radially from an outer periphery thereof;
    a sensing element fixed in the housing; and
    a unitary heat conduction inhibitor formed separately from said housing and disposed to engage a first axial end face of the flange.

2. The gas sensor according to claim 1, further comprising a washer disposed to engage a first axial end of the heat conduction inhibitor.

3. The gas sensor according to claim 1, wherein the heat conduction inhibitor has a ring-shaped structure.

4. The gas sensor according to claim 1, wherein the heat conduction inhibitor has at least one protrusion on a first and/or a second axial end thereof.

5. The gas sensor according to claim 4, wherein the heat conduction inhibitor has at least one radial protrusion.

6. The gas sensor according to claim 5, wherein the heat conduction inhibitor has a plurality of radial protrusions.

7. The gas sensor according to claim 4, wherein the heat conduction inhibitor has at least one axial protrusion.

8. The gas sensor according to claim 7, wherein the heat conduction inhibitor has a plurality of axial protrusions.

9. The gas sensor according to claim 1, wherein the heat conduction inhibitor has at least one groove in an outer periphery thereof.

10. The gas sensor according to claim 9, wherein the heat conduction inhibitor has at least one groove extending circumferentially in an outer periphery thereof.

11. The gas sensor according to claim 9, wherein the heat conduction inhibitor has a single groove.

12. The gas sensor according to claim 9, wherein the heat conduction inhibitor has a plurality of grooves.

13. The gas sensor according to claim 1, wherein the heat conduction inhibitor has at least one protrusion on an outer periphery thereof.

14. The gas sensor according to claim 13, wherein the heat conduction inhibitor has at least one radial protrusion.

15. The gas sensor according to claim 13, wherein the heat conduction inhibitor has a plurality of protrusions.

16. The gas sensor according to claim 1, wherein the heat conduction inhibitor is made of stainless steel.

17. The gas sensor according to claim 1, wherein the heat conduction inhibitor has a coefficient of thermal conductivity that is lower than that of the housing.

18. The gas sensor according to claim 1, wherein the heat conduction inhibitor has a thickness of equal to or greater than 0.2 mm in an axial direction of the housing.

19. The gas sensor according to claim 18, wherein the heat conduction inhibitor has a thickness of equal to or less than 3 mm in an axial direction of the housing.

20. A method of mounting a gas sensor to an exhaust pipe so as to reduce heat conduction from the exhaust pipe through the gas sensor comprising:
    providing a gas sensor comprising a hollow cylindrical housing having a flange which protrudes radially from an outer periphery thereof, and a sensing element fixed in the housing;
    disposing a unitary heat conduction inhibitor formed separately from said housing on a first axial end face of the flange;
    disposing a washer on a first axial end of the heat conduction inhibitor; and
    inserting a first end of the gas sensor into a fitting hole formed in the exhaust pipe so that the washer and the inhibitor are disposed between the exhaust pipe and the flange.

* * * * *